United States Patent
Chang et al.

(10) Patent No.: US 10,369,129 B2
(45) Date of Patent: Aug. 6, 2019

(54) LONG ACTING PHARMACEUTICAL COMPOSITION OF PROTEASE INHIBITOR

(71) Applicant: TaiMed Biologics, Inc., Taipei (TW)

(72) Inventors: James Nienyuan Chang, Newport Beach, CA (US); Hsiang-Fa Liang, New Taipei (TW); Meng-Hsin Chen, Taipei (TW); Kuei-Ling Kuo, Taipei (TW); An-Chieh Li, Keelung (TW)

(73) Assignee: TaiMed Biologics, Inc., Taipei (TW)

( * ) Notice: Subject to any disclaimer, the term of this patent is extended or adjusted under 35 U.S.C. 154(b) by 0 days.

(21) Appl. No.: 15/168,864

(22) Filed: May 31, 2016

(65) Prior Publication Data

US 2017/0340597 A1 Nov. 30, 2017

(51) Int. Cl.
*A61K 31/325* (2006.01)
*A61K 9/00* (2006.01)
*A61K 9/10* (2006.01)
*A61K 9/14* (2006.01)

(52) U.S. Cl.
CPC .......... *A61K 31/325* (2013.01); *A61K 9/0019* (2013.01); *A61K 9/10* (2013.01); *A61K 9/146* (2013.01)

(58) Field of Classification Search
CPC .......... A61K 31/325; A61K 9/14; A61K 47/10
USPC ...................................................... 424/489
See application file for complete search history.

(56) References Cited

U.S. PATENT DOCUMENTS

2006/0287316 A1 12/2006 Wu et al.
2008/0269172 A1 10/2008 Stranix et al.
2009/0176813 A1* 7/2009 Baert ................... A61K 9/0019
                                                    514/275
2009/0253926 A1 10/2009 Milot et al.
2016/0089369 A1 3/2016 Baert et al.

OTHER PUBLICATIONS

Author: Cyndi Root; title: FDA Approves Ibalizumab Manufactured in China by WuXi PharmaTech; News Feature | May 8, 2014; downloaded from https://www.pharmaceuticalonline.com/doc/fda-approves-ibalizumab-manufactured-in-china-by-wuxi-pharmatech-0001 on Jun. 5, 2017.*
Unknown author, title:Highlights of Prescribing Information; downloaded from https://www.accessdata.fda.gov/drugsatfda_docs/label/2012/021752s030lbl.pdf on Sep. 5, 2018. (Year: 2004).*
International Search Report for International Patent Application No. PCT/US2016/035029, dated Sep. 19, 2016 (3 pages).
Written Opinion of the International Searching Authority for International Patent Application No. PCT/US2016/035029, dated Sep. 19, 2016 (6 pages).
International Preliminary Report on Patentability for International Application No. PCT/US2016/035029 dated Dec. 4, 2018 (7 pages).

* cited by examiner

*Primary Examiner* — Yanzhi Zhang
(74) *Attorney, Agent, or Firm* — Clark & Elbing LLP (57) ABSTRACT

Disclosed herein is a long acting pharmaceutical composition for treating or preventing human immunodeficiency virus (HIV) infection. The pharmaceutical composition comprises a suspension of a lysine-based aspartyl protease inhibitor or salt thereof, a surface modifier, and a pharmaceutically acceptable carrier; wherein the lysine-based aspartyl protease inhibitor or salt thereof has an average effective particle size of less than about 500 nm. A method for treating or preventing HIV infection with the pharmaceutical composition is also disclosed.

8 Claims, 4 Drawing Sheets

LONG ACTING PHARMACEUTICAL COMPOSITION OF PROTEASE INHIBITOR

TECHNICAL FIELD OF THE INVENTION

This invention concerns a new pharmaceutical composition of a protease inhibitor providing a long acting effect in inhibition of the activity of HIV aspartyl protease, which is advantageously used to develop a new approach in treatment of HIV. This invention also generally relates to a method for treating HIV.

BACKGROUND OF THE INVENTION

Human immunodeficiency virus (HIV) causes acquired immune deficiency syndrome (AIDS) through infection of specialized cells of the immune system carrying CD4 receptors. The HIV retrovirus reproduces in these cells, especially the so-called T-helper cells, and kills them in the process. While the body has the ability to re-generate T-helper cells to some extent, after years of continuous cell destruction by HIV and fighting back by the immune system, the virus eventually emerges as the battle's winner. The progressive destruction of T-helper cells leads to weakening of the immune system which in turn, opens the door to opportunistic pathogens. When this happens, HIV-infected people start to show clinical symptoms. If left unchecked, HIV infection leads to death in a matter of years.

In order to reproduce in infected cells, HIV needs three major enzymes that are carried inside the viral particle. These three enzymes, reverse transcriptase, protease and integrase, thus represent ideal targets for antiviral therapy. Of these, reverse transcriptase has been the first enzyme targeted by the pharmaceutical industry. Inhibitors of the viral protease have been developed more recently and their use as drugs for AIDS treatment began only in 1996. Although the development of reverse transcriptase and protease inhibitors has improved significantly the survival time and quality of life of HIV-infected patients, their use leads to unwanted side effects, such as anemia, neurotoxicity, bone marrow suppression and lipodystrophy. Most of the currently available anti-protease drugs are large molecules with limited ability to cross the blood-brain barrier.

Some new compounds devoid of these drawbacks have been developed to treat HIV infections, and to fight the resistant viral strains. PCT International Patent Application no. PCT/CA02/00190 (Stranix et al.) published under No. WO 02/064551 HIV disclosed protease inhibitors based on amino acid derivatives. This patent application includes, more particularly, N-amino acid substituted L-lysine derivatives (and analogs) possessing aspartyl protease inhibitory properties. It was also provided some alternate compounds with such properties. For example, U.S. Pat. No. 6,632,816 B1 disclosed a novel class of aromatic derivatives possessing aspartyl protease inhibitory properties, and their biological applications in Treatment of HIV infections.

Long-acting antiretroviral agents are currently under development for the treatment of chronic HIV infection. Long-acting medications could offer an attractive option for people with HIV facing a lifetime of antiretroviral treatment. These agents have the advantage of being more convenient and potentially improving patient's adherence. However, none of previous studies provides a good long acting pharmaceutical composition of a protease inhibitor for treating HIV infection.

SUMMARY OF THE DISCLOSURE

The present invention provides a new approach for treatment or prevention of HIV infection. In various embodiments of the invention, a new long acting pharmaceutical composition of a protease inhibitor and a method for treating HIV infection with the long acting pharmaceutical composition are provided.

In one aspect, the present invention provides a long acting pharmaceutical composition for treating or preventing HIV infection, which comprises a suspension of a lysine-based aspartyl protease inhibitor or salt thereof, a surface modifier, and a pharmaceutically acceptable carrier; wherein the lysine-based aspartyl protease inhibitor or salt thereof has an average effective particle size of less than about 500 nm.

In some preferred embodiments of the invention, the average effective particle size of the lysine-based aspartyl protease inhibitor or salt thereof is preferably less than about 300 nm, more preferably about 200 nm and most preferably between about 100 nm and about 200 nm.

In another aspect, the present invention provides a pharmaceutical composition for administration by intramuscular or subcutaneous injection, which comprises a suspension of a lysine-based aspartyl protease inhibitor or salt thereof, a surface modifier, and a pharmaceutically acceptable carrier; wherein the lysine-based aspartyl protease inhibitor or salt thereof has an average effective particle size of less than about 500 nm.

In a further aspect, the present invention provides a method for treating or preventing HIV infection for long term. The method comprises administering to a subject in need thereof a therapeutically effective amount of the pharmaceutical composition of the invention by intramuscular or subcutaneous injection one a week to a month.

In one or more embodiment, the dose of the suspension is about 5 to about 65 mg/kg of the subject's body weight.

In a yet aspect, the present invention provides a use of a suspension of a lysine-based aspartyl protease inhibitor or salt thereof, a surface modifier, and a pharmaceutically acceptable carrier, for the manufacture of a medicament for the treatment or prevention of HIV infection by intramuscular or subcutaneous injection once a week to a month; wherein the lysine-based aspartyl protease inhibitor or salt thereof has an average effective particle size of less than about 500 nm.

In one or more embodiment, the medicament is administered once a month.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the embodiments.

In the drawings.

DETAILED DESCRIPTION OF THE INVENTION

The present invention has demonstrated for the first time that a new approach for preventing or treating HIV infection by a long acting pharmaceutical composition for administration by intramuscular or subcutaneous injection.

Accordingly, the present invention provides a long acting pharmaceutical composition for treating or preventing HIV infection, which comprises a suspension of a lysine-based aspartyl protease inhibitor or salt thereof, a surface modifier, and a pharmaceutically acceptable carrier; wherein the lysine-based aspartyl protease inhibitor or salt thereof has an average effective particle size of less than about 500 nm, preferably less than about 300 nm, more preferably about 200 nm and most preferably between about 100 nm and about 200 nm.

Lysine-Based Aspartyl Protease Inhibitor

Ambrilia Biopharma Inc. has developed lysine-based aspartyl protease inhibitor having the activity of HIV-1 protease inhibitor, as described in U.S. Pat. No. 6,632,816, which is entirely incorporated herein by reference.

As disclosed in U.S. Pat. No. 6,632,816, the compound has the structure of formula I

I and when the compound of formula I comprises an amino group, pharmaceutically acceptable ammonium salts thereof,
wherein n is 3 or 4,
wherein X and Y, the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_4R_5$, —$NHCOR_4$, —$OR_4$, —$SR_4$, —$COOR_4$, —$COR_4$, and —$CH_2OH$ or X and Y together define an alkylenedioxy group selected from the group consisting of a methylenedioxy group of formula —$OCH_2O$— and an ethylenedioxy group of formula —$OCH_2CH_2O$—,
wherein $R_1$ is selected from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof,
wherein $R_2$ is selected from the group consisting of H, a straight alkyl group of 1 to 6 carbon atoms, a branched alkyl group of 3 to 6 carbon atoms, a cycloalkyl group of 3 to 6 carbon atoms, and a group of formula $R_{2A}$—CO—, $R_{2A}$ being selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, tetrahydro-3-furanyloxy, —$CH_2OH$, —$CF_3$, —$CH_2CF_3$, —$CH_2CH_2CF_3$, pyrrolidinyl, piperidinyl, 4-morpholinyl, $CH_3O_2C$—, $CH_3O_2CCH_2$—, Acetyl-$OCH_2CH_2$—, $HO_2CCH_2$—, 3-hydroxyphenyl, 4-hydroxyphenyl, 4-$CH_3OC_6H_4CH_2$—, $CH_3NH$—, $(CH_3)_2N$—, $(CH_3CH_2)_2N$—, $(CH_3CH_2CH_2)_2N$—, $HOCH_2CH_2NH$—, $CH_3OCH_2O$—, $CH_3OCH_2CH_2O$—, $C_6H_5CH_2O$—, 2-pyrrolyl, 2-pyridyl, 3-pyridyl, 4-pyridyl-, 2-pyrazinyl, 2-quinolyl, 3-quinolyl, 4-quinolyl, 1-isoquinolyl, 3-isoquinolyl, 2-quinoxalinyl, a phenyl group of formula a picolyl group selected from the group consisting of and a picolyloxy group selected from the group consisting of and a substituted pyridyl group selected from the group consisting of and a group selected from the group consisting of wherein X' and Y', the same or different, are selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I,

—CF₃, —NO₂, —NR₄R₅, —NHCOR₄, —OR₄, —SR₄, —COOR₄, —COR₄ and —CH₂OH,
wherein R₄ and R₅, the same or different, are selected from the group consisting of H, a straight alkyl group of 1 to 6 carbon atoms, a branched alkyl group of 3 to 6 carbon atoms, and a cycloalkyl group of 3 to 6 carbon atoms,
wherein R₃ is selected from the group consisting of a diphenylmethyl group of formula IV

IV a naphthyl-1-CH₂— group of formula V

V a naphthyl-2-CH₂— group of formula VI

VI a biphenylmethyl group of formula VII

VII and an anthryl-9-CH₂— group of formula VIII

VIII

As stated in U.S. Pat. No. 6,632,816, one particular embodiment of the compound is of the formula IIa:

IIa

Among the compounds of formula IIa, one compound called as PL-100 (hereinafter called as TMB-607) was confirmed to have effective and selective at inhibiting the HIV-1 protease and a favorable cross-resistance profile having, which is of the structure of the formula IIb:

IIb

It was confirmed in the antiviral studies that TMB-607 was both effective and selective at inhibiting the HIV-1 protease. It was also confirmed in the cross-resistance studies against 63 PI-resistant strains that TMB-607 showed lower levels of reduced susceptibility than any of approved Protease inhibitors (PIs), indicating the potential for good activity against existing PI-resistant viruses in the treatment of experienced patients. A 48-week resistance selection study was performed by increasing the concentrations of TMB-607 against a laboratory-adapted virus in vitro. Four mutations in the protease open reading frame were selected. Site-directed mutagenesis studies indicate that single mutations did not result in significant resistance to TMB-607 in vitro.

However, TMB-607 had a poor solubility, which is not appropriate for a medicament in humans. Accordingly, its phosphorylated pro-drug, called as TMB-657 (former coded PPL-100) having an improved solubility and pharmacokinetic properties had been developed.

In the present invention, a new pharmaceutical composition of a lysine-based aspartyl protease inhibitor or salt thereof, particularly TMB-607, was developed to provide a long acting effect in the treatment or prevention of HIV infection, which can be administered once a week, and even once a month.

Pharmaceutical Composition

The term "pharmaceutically effective amount" refers to an amount effective in treating HIV infection in a patient. It is also to be understood herein that a "pharmaceutically effective amount" may be interpreted as an amount giving a desired therapeutic effect, either taken into one dose or in any dosage or route or taken alone or in combination with other therapeutic agents. In the case of the present invention, a "pharmaceutically effective amount" may be understood as an amount having an inhibitory effect on HIV (HIV-1 and HIV-2 as well as related viruses (e.g., HTLV-I and HTLV-II, and simian immunodeficiency virus)) infection cycle (e.g., inhibition of replication, reinfection, maturation, budding etc.) and on any organism depending on aspartyl proteases for their life cycle.

In addition, this invention provides pharmaceutical compositions in which these novel compounds of formula I, as well as of formulae IIa, and IIb, derived from L-lysine or L-lysine derivatives (as well as its lower homologue (i.e. L-omithine)) are used to inhibit aspartyl proteases, including HIV aspartyl protease, thus providing protection against HIV infection.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "therapeutically effective amount" refers to an amount effective in treating or preventing HIV infection in a subject or a patient.

The terms "pharmaceutically acceptable carrier" refers to a non-toxic carrier or adjuvant that may be administered to a patient, together with a compound of the present invention, and which does not destroy the pharmacological activity thereof.

The compounds of this invention include pharmaceutically acceptable derivatives of the compounds of formula I (as well as of formulae II, IIa, IIb, and IIc) and as applicable pharmaceutically acceptable salts thereof.

As used herein, the term "pharmaceutically acceptable derivative" refers to any pharmaceutically acceptable salt, ester, or salt of such ester, of a compound of this invention or any other compound which, upon administration to a recipient, is capable of providing (directly or indirectly) a compound of this invention or an antivirally active metabolite or residue thereof.

According to the invention, the pharmaceutically acceptable salts of the compounds of this invention include those derived from pharmaceutically acceptable inorganic and organic acids and bases. Examples of such acid salts include: acetate, adipate, alginate, aspartate, benzoate, benzenesulfonate, bisulfate, butyrate, citrate, camphorate, camphorsulfonate, cyclopentanepropionate, digluconate, dodecylhydrogensulfate, dodecylsulfate, ethanesulfonate, formate, fumarate, glucoheptanoate, glycerophosphate, glycollate, hemisulfate, heptanoate, hexanoate, hydrochloride, hydrobromide, hydroiodide, 2-hydroxyethanesulfonate, lactate, maleate, malonate, methanesulfonate, 2-naphthylsulfonate, nicotinate, nitrate, oxalate, pamoate, pectinate, perchlorate, persulfate, 3-phenylpropionate, phosphate, picrate, pivalate, propionate, salicylate, succinate, sulfate, tartrate, thiocyanate, tosylate, and undecanoate.

With respect to the number of carbon atoms, the mention of the range of 1 to 6 carbon atoms is to be understood herein as incorporating each and every individual number of carbon atoms as well as sub-ranges such as, for example, 1 carbon atoms, 3 carbon atoms, 4 to 6 carbon atoms, etc.

According to the present invention, the prepare the long acting pharmaceutical composition can be prepared by any commonly used and known methods by admixing the lysine-based aspartyl protease inhibitor or salt thereof in an appropriate particle size, with an appropriate surface modifier, and one or more appropriate pharmaceutically acceptable carriers.

In the invention, the surface modifier is selected from the group consisting of poloxamers, alpha-tocopheryl polyethylene glycol succinates, polyoxyethylene sorbitan fatty acid esters, and phospholipids. Preferably, the surface modifier is selected from the group consisting of poloxamer 188, poloxamer 407, d-α-Tocopheryl polyethylene glycol 1000 succinate (simply TPGS or Vitamin E TPGS), Tween 80, and distearoylphosphatidylethanolamine-poly(ethylene glycol) (DSPE-PEG), which are supported by the examples shown in Table 1.

Methods of Treatment and Prevention

According to the invention, the long acting pharmaceutical composition disclosed herein are employed for the treatment and/or prevention of HIV infection in a subject, as well as prevention of HIV transmission.

The term "treatment" of HIV infection refers to effective inhibition of the HIV infection so as to delay the onset, slow down the progression, reduce viral load, and/or ameliorate the symptoms caused by HIV infection.

The term "prevention" of HIV infection means the onset of HIV infection is delayed, and/or the incidence or likelihood of HIV infection is reduced or eliminated.

The term "prevention" of HIV transmission means the incidence or likelihood of HIV being transmitted from one individual to another (e.g., from an HIV-positive woman to the child during pregnancy, labor or delivery, or breastfeeding; or from an HIV-positive subject to an HIV-negative partner) is reduced or eliminated.

The term "subject" or "patient" refers to any primate subject, including human and non-human subjects (e.g., rhesus subjects).

To treat and/or prevent HIV infection, a therapeutic amount of the pharmaceutical composition disclosed herein is administered to a subject in need.

The term "therapeutically effective amount" means the dose required to effect an inhibition of HIV infection so as to treat and/or prevent HIV infection. The dosage of an antibody depends on the disease state and other clinical factors, such as weight and condition of the subject, the subject's response to the therapy. The precise dosage to be therapeutically effective and non-detrimental can be determined by those skilled in the art. In one embodiment of the invention, a suitable dose of the long acting pharmaceutical composition for intramuscular or subcutaneous administration to adult humans is in the range of about 5 to about 65 mg/kg of subject's body weight once a week, or even once a month.

Long Acting Effect of the Pharmaceutical Composition According to the Invention

Figure 1:
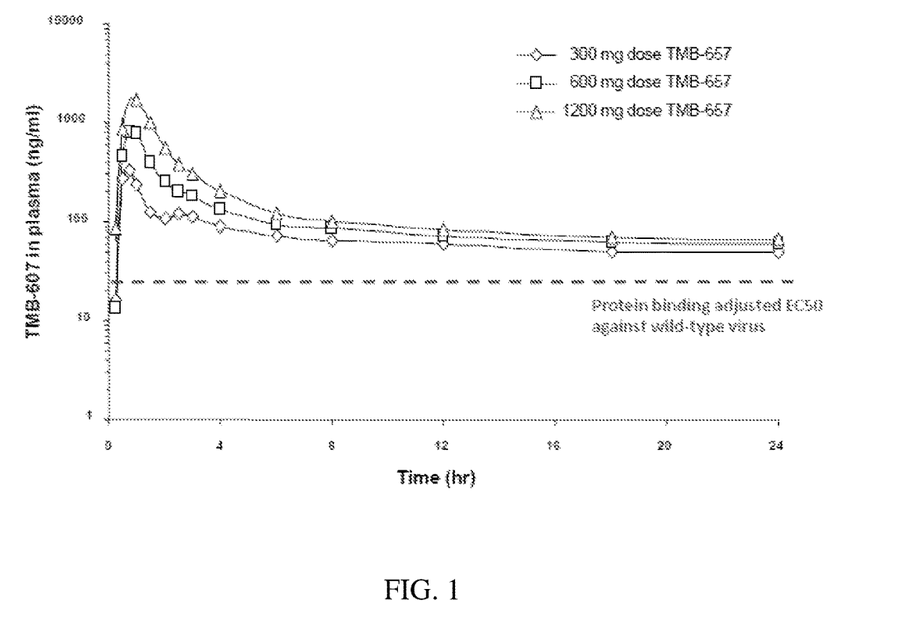
FIG. 1 shows the PK profiles of TMB-607 in humans administrated with TMB-657 in the oral form.
Figure 2:
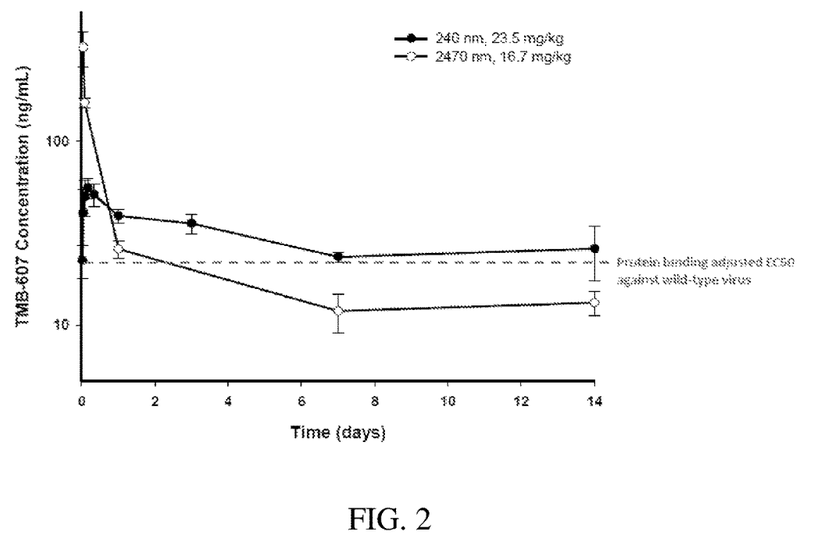
FIG. 2 shows the PK profiles of TMB-607 in rats administrated with TMB-607 in the forms of micro-particles (2470 nm) and nano-suspension (240 nm) respectively.

According to the invention, it is confirmed in the examples that the suspension of TMB-607, one example of the lysine-based aspartyl protease inhibitor, a surface modifier, and a pharmaceutically acceptable carrier, provide a long acting effect, wherein the lysine-based aspartyl protease inhibitor or salt thereof has an average effective particle size of less than about 500 nm. As demonstrated in Example 3, the plasma levels of TMB-607 in the group treated with the TMB-607 in the form of nano-suspension (247 nm) by a subcutaneous administration maintained for more than 14 days, as compared with those in the group treated with the TMB-607 in the form of microparticle (2470 nm), see FIG. 2. It was indicating that nanosized TMB-607 could prolong the plasma level above the protein binding adjusted EC50 for 14 days, but TMB-607 microparticles did not.

Figure 3:
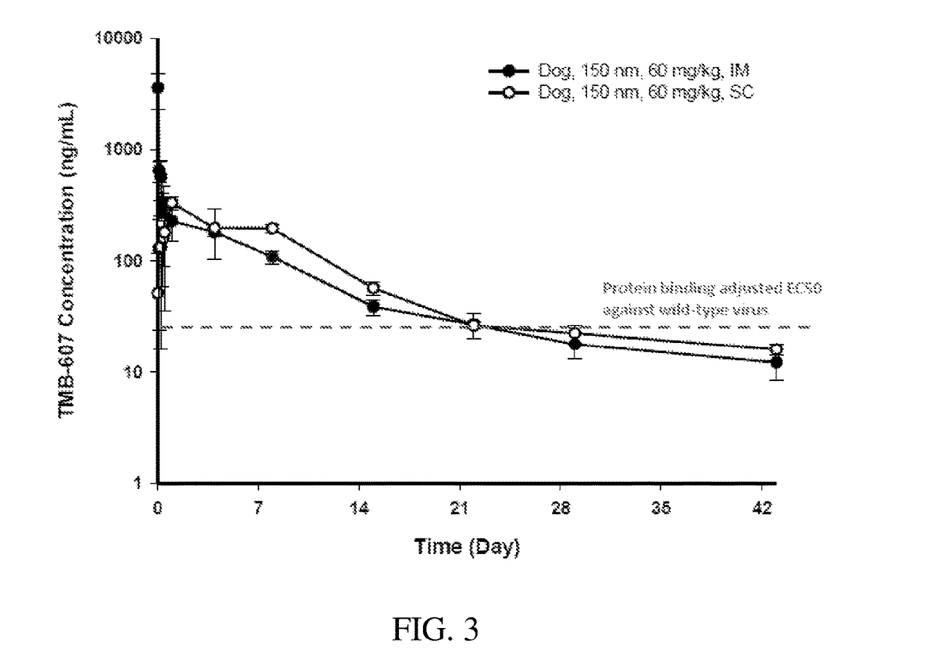
FIG. 3 shows the plasma levels of TMB-607 in beagle dogs after subcutaneous (SC) and intramuscular (IM) injections respectively.
Figure 4:
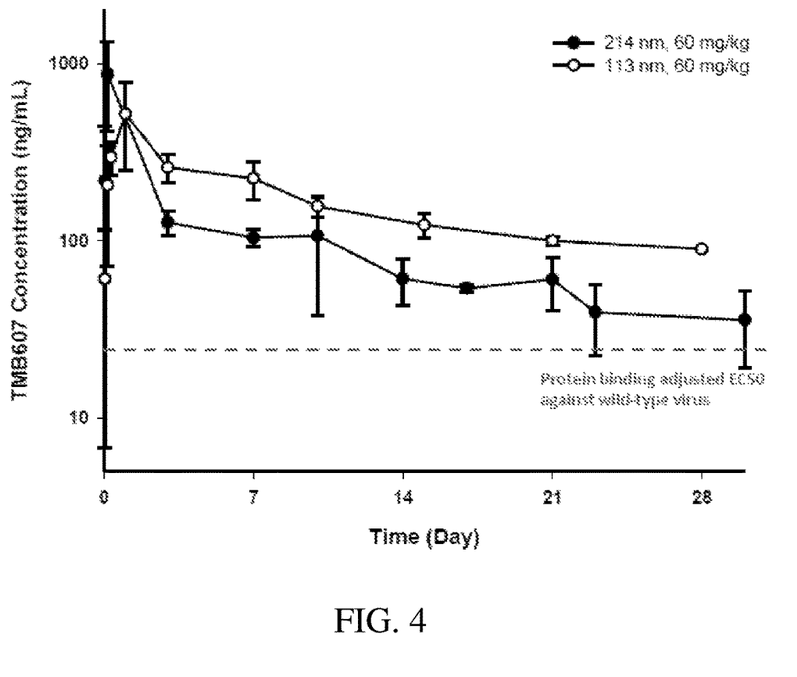
FIG. 4 shows the plasma levels of TMB-607 in monkeys administrated with the TMB-607 in the form of nano-suspension in different particle sizes (240 nm and 113 nm).

It was also confirmed in Example 4 that the animals after treated with a single intramuscular or subcutaneous injection of the TMB-607 in the form of nano-suspension had prolonged plasma levels of TMB-607, see FIG. 3. Furthermore, it was demonstrated in Example 5 that both the particle size of 214 nm and that of 113 nm could prolong the plasma levels, and the smaller size of TMB-607 (113 nm) possessed the higher plasma level and longer effective duration.

EXAMPLES

Example 1 Preparation of Nano-Suspension of TMB-607

To prepare the nano-suspension by wet ball-milling process, TMB-607 was added into an aqueous polymer solution with a 1:1 to 7:1 drug to polymer ratio (D/P ratio, by w/w). The suspension mixture was then poured into Delta Vita 15-300 (DV-15, Netzsch Premier Technologies, USA-Exton, Pa.), which was partially filled with 0.1-3 mm $ZrO_2$ grinding beads in the grinding chamber. The suspension mixture was ground at various speeds and for approximately 6 hours to 7 days until the mean particle size reached submicron range. When the wet ball-milling process was completed, the drug concentration of the nanonized suspension mixture was adjusted by WFI. Following the concentration adjustment, tonicity agent was added to adjust the osmolality of the suspension mixture to 300 mOsm/kg. The final concentration of TMB-607 for injectable suspension DP was in the range 20 mg/ml-400 mg/ml. Their particle size of various formulation analyzed by a dynamic light scattering equipment (Zetasizer Nano S, Malvern) were around 100 nm-500 nm. The formulations of the nano-suspension of TMB-607 as obtained was summarized in Table 1 below.

TABLE 1

Composition, concentration and particle size of the nano-suspensions of TMB-607

| Surfactant used | D/P ratio | Bead diameter (mm) | Drug concentration (mg/ml) | Particle size (nm) |
|---|---|---|---|---|
| TPGS | 1/1 | 3 | 20 | 294.3 |
| DSPE-PEG2000 | 1/1 | 3 | 20 | 276.0 |
| Poloxamer 407 | 1/1 | 3 | 20 | 243.5 |
| Poloxamer 407 | 4/1 | 3 | 20 | 233.8 |
| Poloxamer 407 | 4/1 | 3 | 100 | 216.4 |
| Poloxamer 407 | 4/1 | 3 | 240 | 210.4 |
| Poloxamer 407 | 4/1 | 3 | 300 | 190.5 |
| Poloxamer 188 | 4/1 | 3 | 300 | 350.5 |
| Tween-80 | 4/1 | 3 | 300 | 187.3 |
| Poloxamer 407 | 4/1 | 1 | 300 | 190.1 |
| Poloxamer 407 | 4/1 | 0.5 | 200 | 146.8 |
| Poloxamer 407 | 4/1 | 0.1 | 200 | 143.6 |
| Poloxamer 407 | 5/1 | 0.1 | 200 | 113.0 |
| Poloxamer 407 | 7/1 | 0.1 | 200 | 126.5 |

Example 2 Pharmacokinetic Study of Oral Form TMB-657

A first-in-man single-dose escalation study of oral formulation TMB-657 was conducted at doses 300, 600 and 1200 mg. Six subjects received a single dose of TMB-657. The clinical pharmacokinetic profiles of TMB-607 was obtained in the patients with the single-dose escalation of TMB-657 in relation to its protein binding-adjusted antiviral activity (EC50=23 ng/ml). As shown in FIG. 1, oral TMB-657 single dose could maintain the TMB-607 plasma level above the effect level (protein binding EC50, 23 ng/ml) for 24 hours. [Kazmierski, *Antiviral drugs: from basic discovery through clinical trials*, Chapter 2 Page 19, John Wiley & Sons, Inc, 2011.]

Example 3 Pharmacokinetic Studies for TMB-607 in the Forms of Microparticles and Nano-Suspension The studies demonstrated that an injectable formulation of nanonized TMB-607 results in stable blood plasma levels during a prolonged period of time (more than 1 month). In a rat study, TMB-607 in the forms of microparticle (2470 nm) and nano-suspension (240 nm) were subcutaneously administrated at a dose of 16.7 and 23.5 mg/kg, respectively. The results were shown in FIG. 2, indicating that nanosized TMB-607 could prolong the plasma level above the protein binding adjusted EC50 for 14 days, but TMB-607 microparticles did not. In addition, a dramatic high Cmax observed in the group treated with the TMB-607 in the form of microparticles in the initial time period, which would cause significant side effects to human body. In contrast, TMB-607 in the form of nanosuspension presented a sustained release profile in the study period.

Experiment 4 Comparison Between Intramuscular and Subcutaneous Injections

A dog study was conducted to compare the pharmacokinetics of TMB-607 after a single intramuscular or subcutaneous injection of the nano-suspension. Each treatment group consisted of 3 male Beagle dogs at a dose of 60 mg/kg. The particle size used in this study was around 150 nm, and the plasma levels of TMB-607 were monitored for 6 weeks. As shown in FIG. 3, no significant difference was observed in the AUC0-t values between the dogs treated with TMB-607 at 60 mg/kg via two dosing routes: a subcutaneous and intramuscular administration, while the Cmax values for the intramuscular dosing route were higher than those for the subcutaneous dosing route.

Example 5 Plasma Levels of TMB-607 in Monkeys Administrated with the Nano-Suspensions in Different Particle Sizes In a monkey pharmacokinetic study, the nano-suspension of TMB-607 at the different particle sizes of 214 nm and 113 nm were injected into monkeys respectively. Each treatment group consisted of 3 monkeys at a dose of 60 mg/kg. FIG. 4 shows the plasma levels of TMB-607 monitored for 4 weeks. Comparing the different particle size of administration of TMB-607 at 60 mg/kg, both AUC0-t and $t_{1/2}$ generally increased while decreasing the particle size of TMB-607 nano-suspensions. The results were shown in FIG. 4, indicating that the smaller size of TMB-607 particle possesses the higher plasma level and longer effective duration.

CONCLUSION

The present invention provides a suspension of a lysine-based aspartyl protease inhibitor or salt thereof, a surface modifier, and a pharmaceutically acceptable carrier; wherein the lysine-based aspartyl protease inhibitor or salt thereof has an average effective particle size of less than about 500 nm, which can be developed to a long acting pharmaceutical composition for treatment or prevention of HIV infection.

What is claimed is:

1. A long acting pharmaceutical composition for treating human immunodeficiency virus (HIV) infection, which consists of a suspension of a lysine-based aspartyl protease inhibitor or salt thereof, a surface modifier, wherein the surface modifier is selected from the group consisting of poloxamer 188, poloxamer 407, d-α-Tocopheryl polyethylene glycol 1000 succinate (TPGS or Vitamin E TPGS), Polysorbate 80 (Tween 80), and distearoyl phosphatidylethanolamine-poly(ethylene glycol) (DSPE-PEG), and a pharmaceutically acceptable carrier; wherein the lysine-based aspartyl protease inhibitor is TMB-607 having the structure of formula IIb:

and
wherein the average effective particle size of the lysine-based aspartyl protease inhibitor or salt thereof is 300 nm or less.

2. The pharmaceutical composition of claim 1, wherein the composition is formulated for intramuscular or subcutaneous injection.

3. A method of treating HIV infection for a long term comprising administering to a subject in need thereof by intramuscular or subcutaneous injection once a week to once a month a therapeutically effective amount of a pharmaceutical composition consisting of a suspension of a lysine-based aspartyl protease inhibitor or salt thereof, a surface modifier, and a pharmaceutically acceptable carrier; wherein the lysine-based aspartyl protease inhibitor or salt thereof has an average effective particle size of less than 300 nm, and wherein the lysine-based aspartyl protease inhibitor is TMB-607 having the structure of formula IIb:

4. The method of claim 3, wherein a dose of the pharmaceutical composition of about 5 to about 65 mg/kg of the subject's body weight is administered.

5. The method of claim 3, wherein the administering is by intramuscular injection.

6. The method of claim 3, wherein the administering is by subcutaneous injection.

7. The method of claim 1, wherein the average effective particle size of the lysine-based aspartyl protease inhibitor or salt thereof is 240 nm or less.

8. The method of claim 3, wherein the lysine-based aspartyl protease inhibitor or salt thereof has an average effective particle size of less than 240 nm.

* * * * *